(12) United States Patent
Kreitenberg

(10) Patent No.: US 8,193,515 B2
(45) Date of Patent: Jun. 5, 2012

(54) SPORTS BALL STERILIZER

(76) Inventor: Arthur Kreitenberg, Los Angeles, CA (US)

( * ) Notice: Subject to any disclaimer, the term of this patent is extended or adjusted under 35 U.S.C. 154(b) by 151 days.

(21) Appl. No.: 12/814,156

(22) Filed: Jun. 11, 2010

(65) Prior Publication Data
US 2011/0079732 A1   Apr. 7, 2011

Related U.S. Application Data

(60) Provisional application No. 61/249,028, filed on Oct. 6, 2009.

(51) Int. Cl.
*A61L 2/10* (2006.01)
*H01J 37/20* (2006.01)

(52) U.S. Cl. .................. 250/455.11; 250/504 R; 422/24

(58) Field of Classification Search ............. 250/455.11, 250/493.1–504 R; 422/22, 24
See application file for complete search history.

(56) References Cited

U.S. PATENT DOCUMENTS

| | | | |
|---|---|---|---|
| 5,361,440 A | 11/1994 | Buchbinder et al. | |
| 5,369,892 A | 12/1994 | Dhaemers | |
| 5,673,918 A | 10/1997 | Bigari | |
| 6,311,974 B1 | 11/2001 | Koga | |
| 6,389,639 B1 | 5/2002 | Worsham | |
| 6,753,536 B2 * | 6/2004 | Humphreys et al. | 250/455.11 |
| 6,779,714 B2 | 8/2004 | Webb | |
| 6,889,449 B2 | 5/2005 | Silver | |
| 6,992,301 B2 | 1/2006 | Fenc | |
| 7,397,041 B1 * | 7/2008 | Leonard | 250/455.11 |
| 2002/0168287 A1 * | 11/2002 | Eckhardt et al. | 422/24 |
| 2005/0159275 A1 | 7/2005 | Bullman et al. | |
| 2008/0000036 A1 * | 1/2008 | Yun | 15/21.2 |
| 2009/0193676 A1 | 8/2009 | Shengguang et al. | |
| 2009/0252646 A1 * | 10/2009 | Holden et al. | 422/24 |

FOREIGN PATENT DOCUMENTS

| | | |
|---|---|---|
| JP | 10057614 | 3/1998 |
| JP | 2000325059 | 11/2000 |
| JP | 2007082747 | 4/2007 |
| JP | 2009291349 | 12/2009 |
| KR | 10-0567660 | 4/2006 |
| KR | 20-0418460 | 6/2006 |
| KR | 10-0611925 | 8/2006 |

OTHER PUBLICATIONS

PCT International Search Report for PCT/US2010/051296, dated Jun. 3, 2011.

* cited by examiner

*Primary Examiner* — Jack Berman
*Assistant Examiner* — David E Smith
(74) *Attorney, Agent, or Firm* — Greenberg Traurig, LLP

(57) ABSTRACT

A system for sterilizing a sports ball comprises a housing; a door for the housing for opening and closing the housing and for permitting manual location of a ball in the housing; a sterilizing light for sterilizing a ball placed in the housing. The ball is rotatable in the housing such that the surface of the ball is exposed to the light. An elongated track extends from one end of the housing towards another end, and the light can be elongated from one end towards another end. There can be a support pivot on an outer surface of the housing permits the housing to be rocked about the pivot. There can be a series of rollers and one of the rollers can be motorized to rotate a ball. An outlet from the housing is directed to a tray for receiving a sterilized ball. The housing can include an internal surface with a light reflective material.

28 Claims, 10 Drawing Sheets

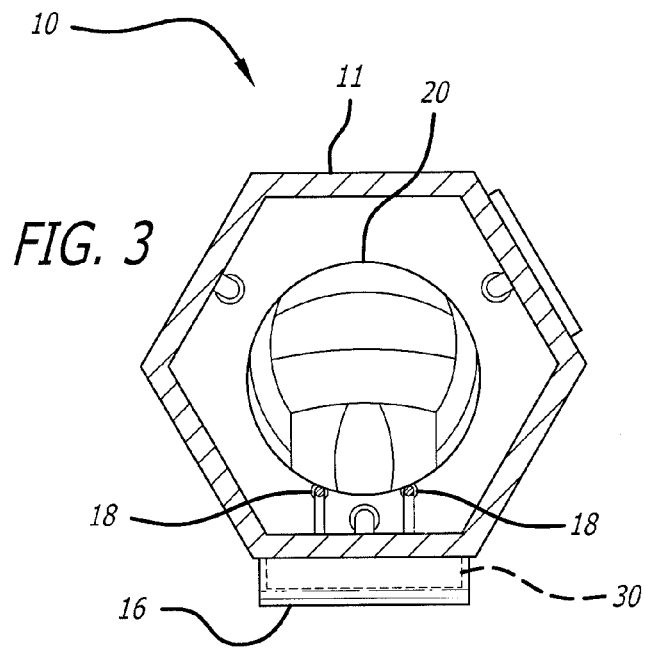
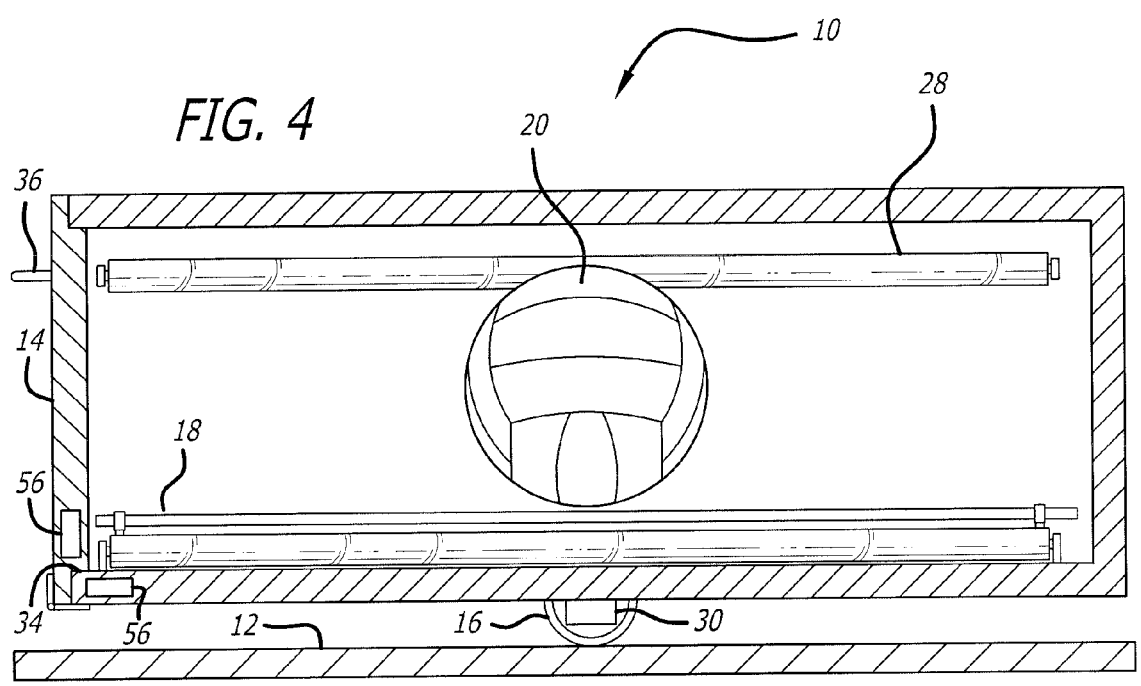

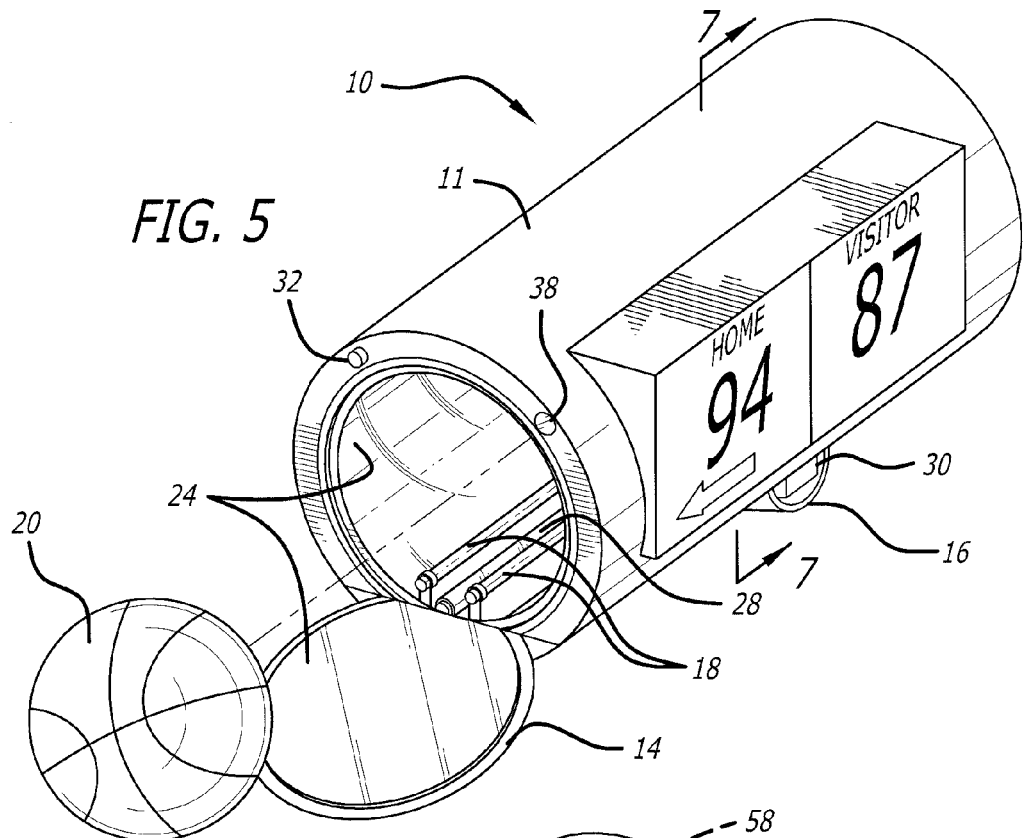
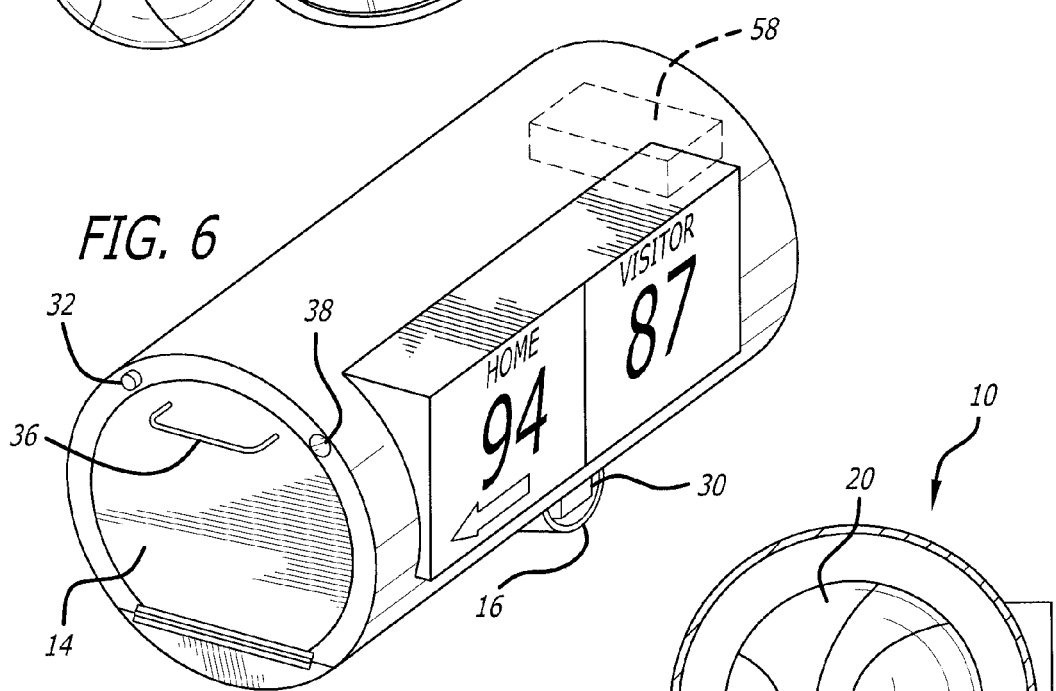
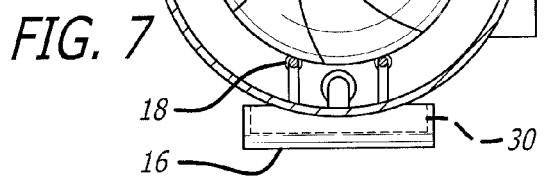

FIG. 8A
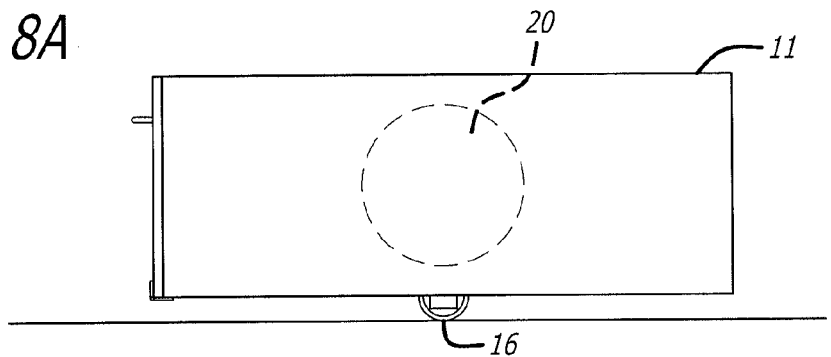
FIG. 8B
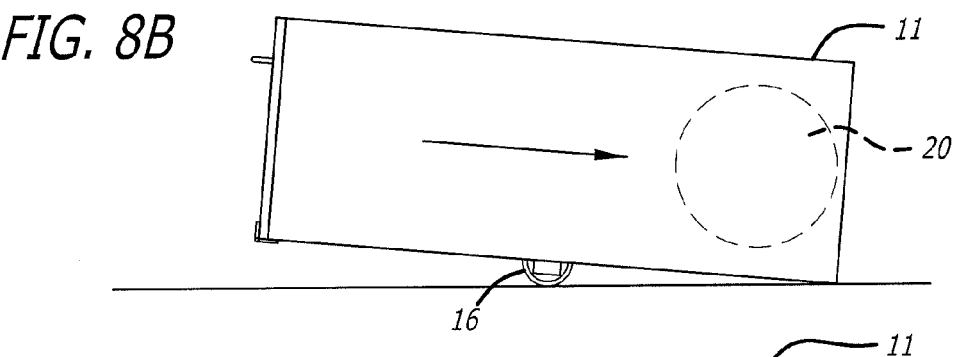
FIG. 8C
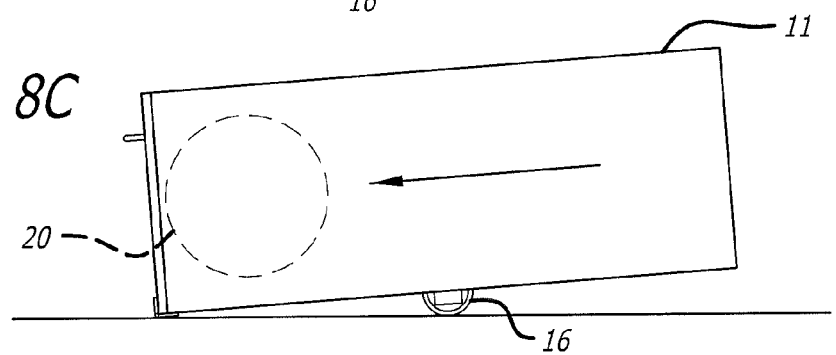
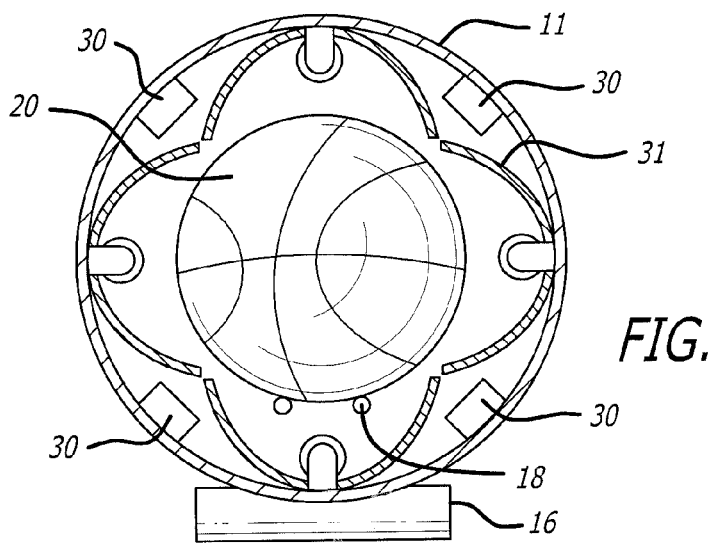
FIG. 9

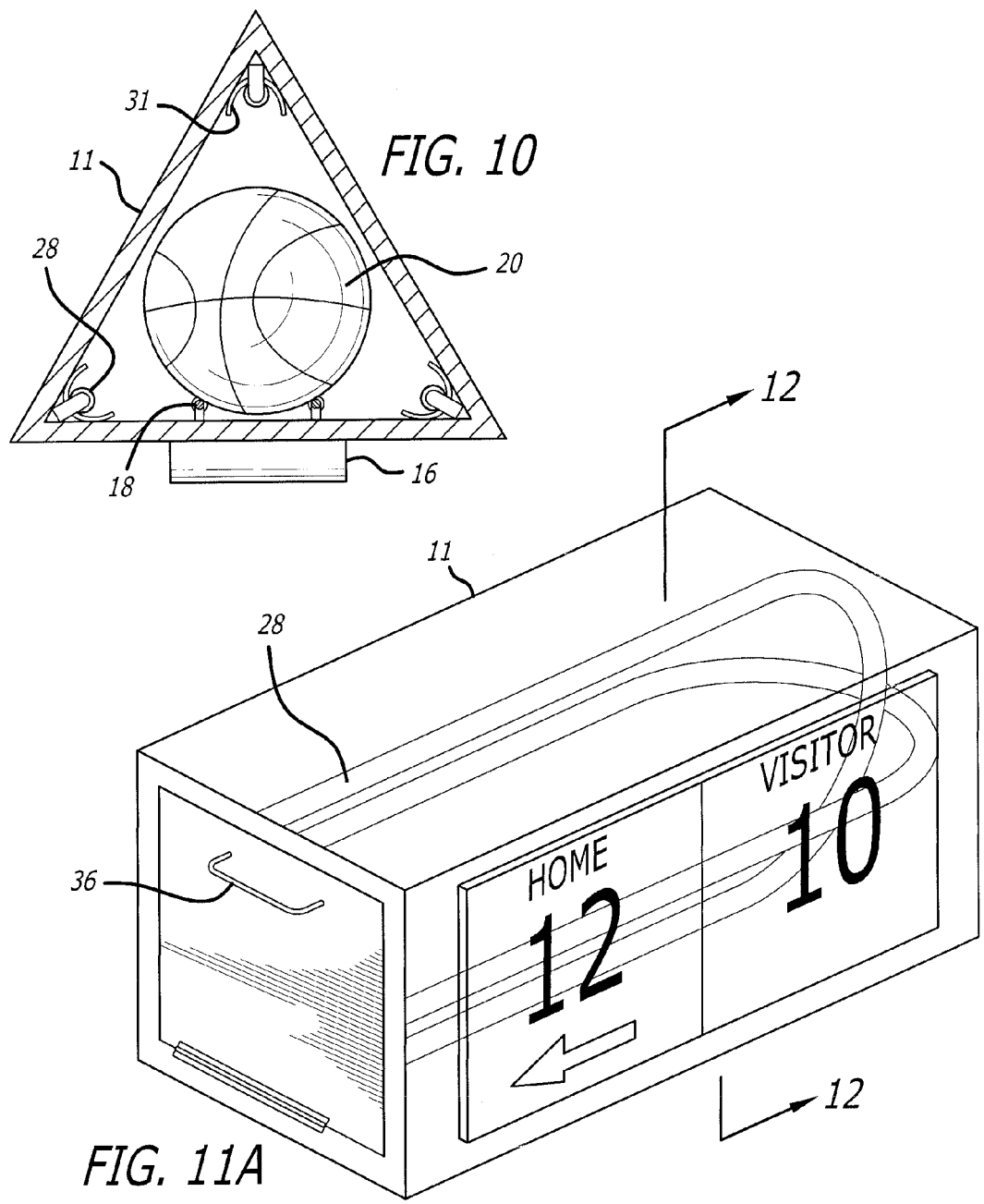
FIG. 10
FIG. 11A
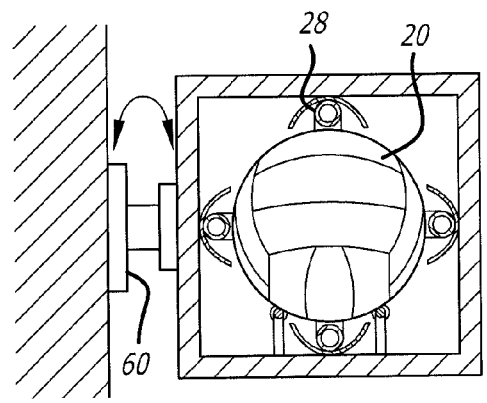
FIG. 12

SPORTS BALL STERILIZER

RELATED APPLICATION

This application claims the benefit of and priority to U.S. Provisional Application Ser. No. 61/249,028, filed Oct. 6, 2009, the contents of which are incorporated by reference herein in its entirety.

BACKGROUND

1. Field

This disclosure relates to the light sterilization of rollable objects that may serve as conduits (fomites) for transfer of germs, such as balls used for sport.

2. General Background

The current disclosure successfully solves a potentially life threatening problem that has been recognized for several years, but heretofore considered unsolvable. This disclosure provides an unanticipated and critical need to prevent the transmission of disabling and potentially fatal infectious diseases among those participating in sports. Those skilled in the art never appreciated the advantages of the current disclosure although this is inherent. Athlete to athlete disease transmission has been recognized for decades, yet no description exists of sterilizing the ball used in sports. Furthermore, the emergence of antibiotic resistant organisms makes this disclosure an important advance.

Infectious disease transmission among persons in athletics and related endeavors is a significant and increasing health concern. Common and potentially serious viral (e.g. influenza-H1N1, HIV, herpetic), bacterial (e.g. Methicillin Resistant Staph Aureus, "flesh eating" Streptococcus) and fungal infections can rapidly spread through direct human to human contact as well as shared frequently touched surfaces. The scientific term "fomite" refers to an inanimate object to which pathogens can adhere and thus be transferred from one person to another. Multiple studies have shown these common pathogens survive for days on common fomites in typical indoor ambient conditions.

The sports ball is the ultimate fomite, where repetitive touching of its surface by multiple persons in rapid succession is mandatory to achieve the very object of the game.

The National Institutes of Health (NIH)/Center for Disease Control (CDC) have collaborated with the National Collegiate Athletic Association (NCAA) in an educational awareness program on this important topic. Frequent hand washing, covering of wounds, and avoidance of exposure to blood and sweat are advocated as cornerstones of prevention of germ transmission and disease. Sweat, blood, saliva, phlegm and nasal discharges are common in the athletic environment and shared surfaces, including the ball, provide ideal pathogen carrier and transmission means.

Focused observation of a sporting event, such as basketball or volleyball readily demonstrates how rapidly and efficiently the touch of a ball by a single contaminated player, coach or official can spread organisms. A participant wipes their sweat, rubs their nose or touches an abrasion or wound, unintentionally placing germs onto their hands, even if cleaned one minute earlier. They then pass, serve, bounce, shoot, hit or otherwise contact the ball, again transferring those germs to the ball, which is already covered with bodily fluids and dirt on a surface readily adherent for germs. The next player receives not only the ball, but also receives the germs of the last player and all the other players who have touched the ball in the previous days.

Hand washing is helpful, but cannot be sufficient in a sports environment.

Following the practice, game or match, balls are typically placed in a storage cage, bag or cart, touching multiple other balls, and stored in a dark, warm room or vehicle. The sweat, blood and dirt residues on the balls provide optimal germ replicating conditions, ready for the next ball use.

The ball is but one surface commonly touched by and shared by athletes. Other surfaces that can serve as fomites include benches, tables, the floor, cafeterias and restrooms. The visual presence of the disclosure serves as a reminder and increases awareness among sports participants of the importance of good hygiene to prevent the spread of disease.

There is a need for improving the hygiene with and about sports balls

SUMMARY

This disclosure provides a means of conveniently, safely and effectively sterilizing rollable objects including sports balls, such as volleyballs and basketballs utilizing Ultraviolet light, in the germicidal wavelength, commonly referred to as the "C" band (UVC).

Prior to this disclosure there has been no description of any device for sterilizing such balls, although the need is acute and evident.

A regulation basketball has an estimated 30,000 "dimples" on its surface. It is therefore desirable to provide some relative motion between the ball and the UVC source to ensure that every side of every dimple is exposed to UVC and no "shadows" remain where germs can hide and survive. Similarly, stitching, panel seams, logos and labels provide multiple crevices, pits, hills and valleys on a stationary ball surface that could provide "safety shadows" for germ survival.

The disclosure is intended to be used prior to, during and after a practice or competition. Depending upon the configuration of the embodiment, a ball can be sterilized in seconds. Thus, during a brief time out, end of period/quarter/game/match, the balls can be re-sterilized so that player safety is always maximized. Hands and balls can become quickly re-contaminated. Just as frequent hand washing is effective, frequent ball sterilization is simply the logical extension.

According to the disclosure, an autoclave device is described for rapidly and efficiently sterilizing balls used for sport to prevent disease transmission among ball handling participants.

According to the disclosure, a housing/enclosure contains the object to be sterilized, for example, a volleyball or basketball, a source(s) of germicidal ultraviolet light, and a system of exposing all surfaces of the object to said light. The system involves relative motion between the object and light source(s). The housing/enclosure is impenetrable to the germicidal light, as such light can also be harmful to humans.

DRAWINGS

The above-mentioned features and objects of the present disclosure will become more apparent with reference to the following description taken in conjunction with the accompanying drawings wherein like reference numerals denote like elements and in which:

FIG. 1 is a perspective view of a first embodiment with the door open. Note the device is tilted so the door end of the housing/enclosure is down, so the ball rolls toward the opened end of the housing/enclosure and out of the opened end. The embodiment is a Table Top-External Pivot version.

FIG. 3 is a sectional view along line 3-3 of a first embodiment showing a ball in place.

FIG. 4 is a sectional view along line 4-4 of a first embodiment showing a ball in place.

FIG. 5 is a perspective view of a cylindrical housing enclosure with the door open. Note the device is tilted so the door end of the housing/enclosure is down, so the ball rolls toward the opened end of the housing/enclosure and out of the opened end. The embodiment is a different variation of a Table Top-External Pivot version. A display is shown on the outside wall of the housing.

FIG. 6 is a perspective view of the embodiment of FIG. 5 with the door closed. A display is shown on the outside wall of the housing. A battery pack power source is demonstrated.

FIG. 7 is a sectional view along line 7-7 of the embodiment of FIG. 5 showing a ball in place.

FIG. 8A is a representative side view of the device in a horizontal level position and showing the ball inside the housing and centered in the device of the first embodiment.

FIG. 8B is a representative side view showing the ball inside the housing and the device in a tilted position such that the ball is adjacent the non-door end in the device of the first embodiment.

FIG. 8C is a representative side view showing the ball inside the housing and the device in an opposite tilted position such that the bail is adjacent the door end in the device of the first embodiment.

FIG. 9 is an end sectional view of a further variation of the first embodiment showing a ball in place, and there being several longitudinal sterilizing lamps arranged around the inside perimeter of the housing. Parabolic reflectors maximize ball exposure and protect the sterilizing lamps from an errant ball. Such an internal configuration may also be used with the embodiment of FIGS. 18-21.

FIG. 10 is an end sectional view of another variation of the first embodiment showing a ball in place, and there being several longitudinal sterilizing lamps arranged around the inside perimeter of the housing.

FIG. 11A is a perspective view using "U" shaped bulbs of a second embodiment with the door closed.

Figure 11B:
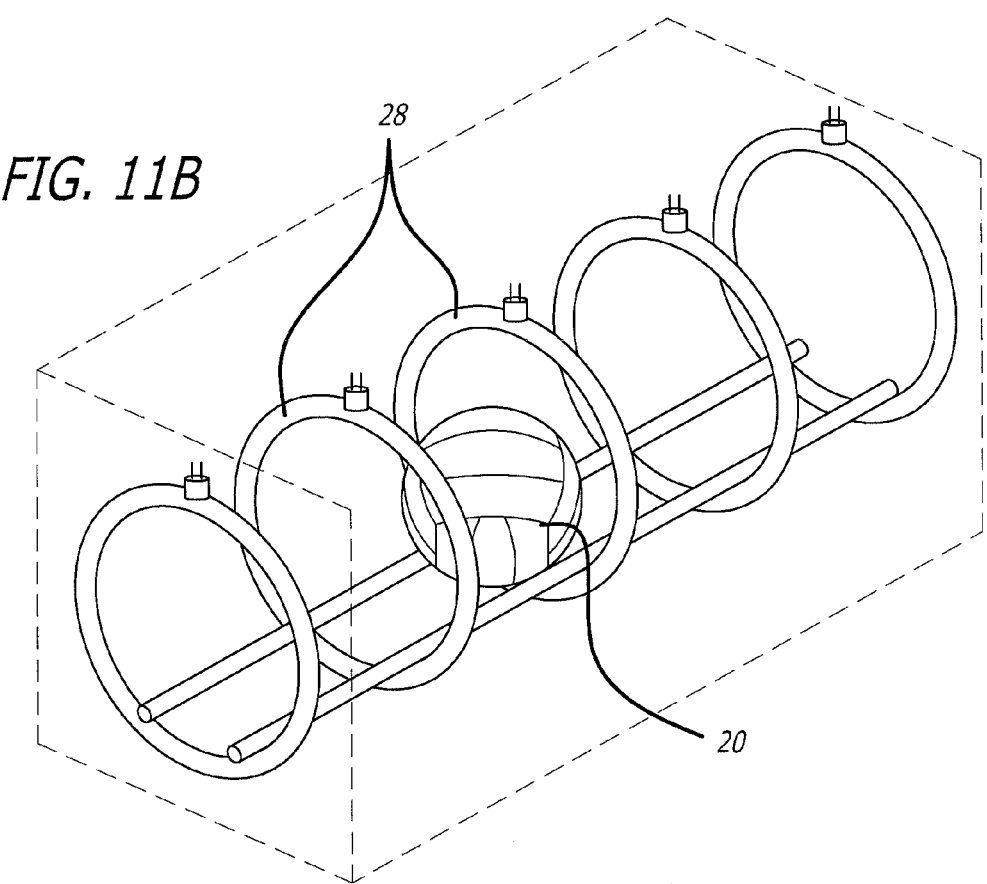

FIG. 11B shows a series of lights that are circular.

Figure 11C:
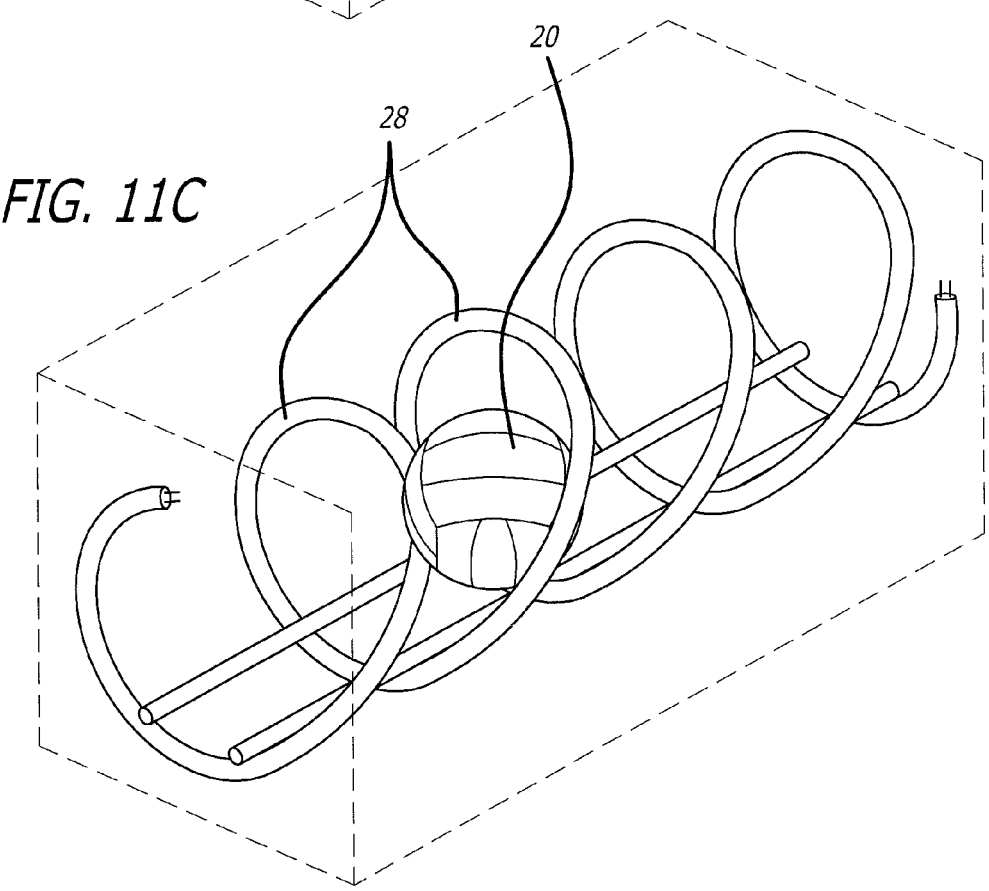

FIG. 11C shows a light that follows a helical path.

FIG. 12 is an end sectional view of another variation of the second embodiment showing a ball in place, and there being several longitudinal sterilizing lamps arranged around the inside perimeter of the housing. This embodiment uses a wall mounted pivot mechanism with limiting stops at angles sufficient to allow ball rolling with the housing.

Figure 13:
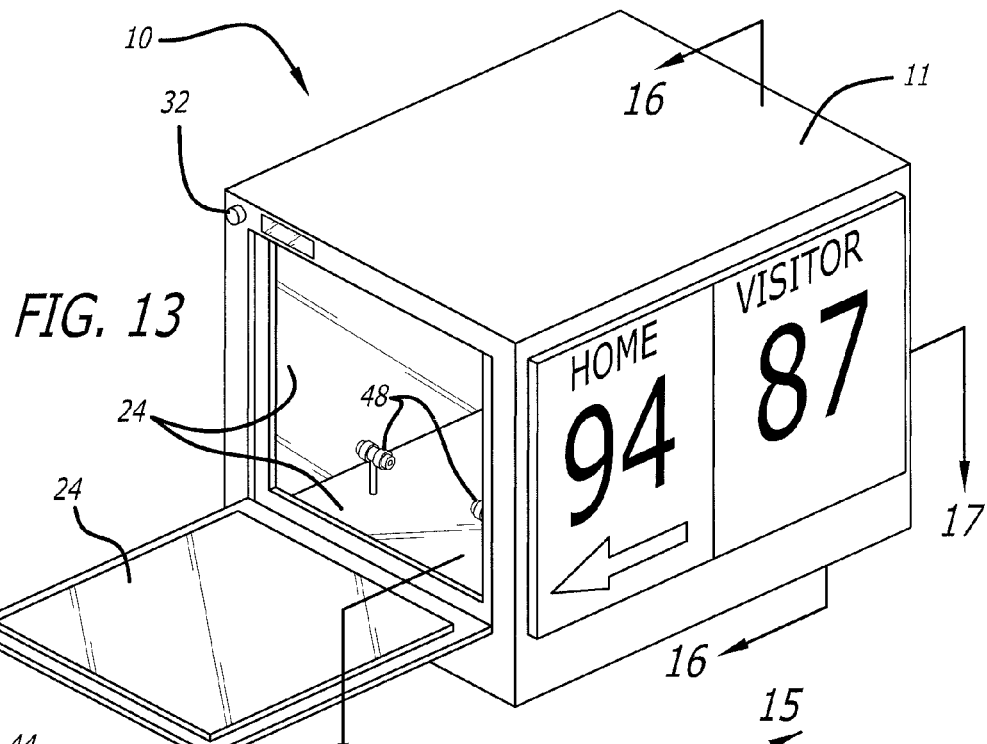

FIG. 13 is a perspective view of a second embodiment. This is a Table Top-Internal Roller embodiment, shown with the door open. This embodiment does not tilt, but the ball is rotated by mechanized means within a more compact housing/enclosure.

Figure 14:
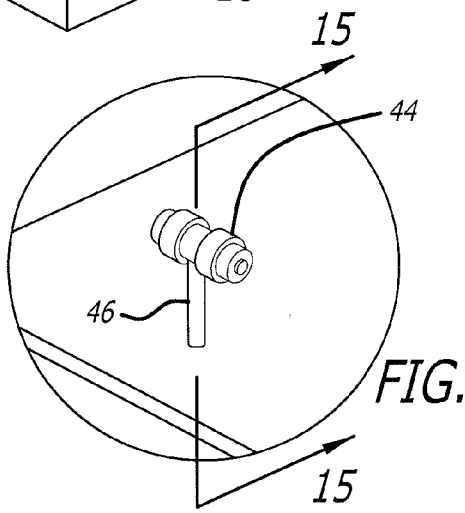

FIG. 14 is a detail of one of the rollers of the embodiment of FIG. 13.

Figure 15:
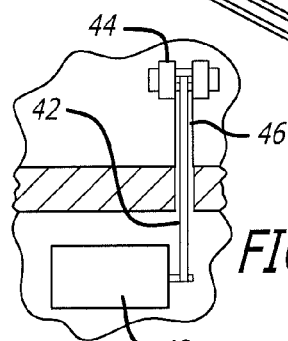

FIG. 15 is another detail view of a drive roller with motor and drive belt within the column.

Figure 16:
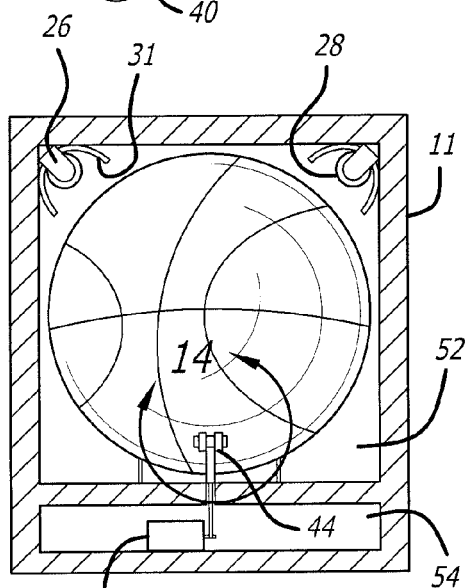

FIG. 16 is an end sectional view along line 16-16 of the variation of the FIG. 13 embodiment showing a ball in place, and there being several longitudinal sterilizing lamps and reflectors arranged around the inside perimeter of the housing, and rollers for the ball.

Figure 17:
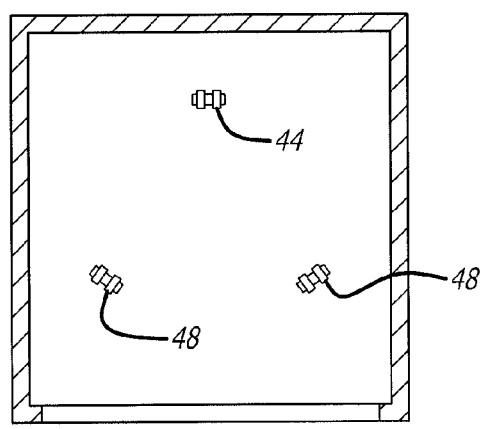

FIG. 17 is a bottom view along line 17-17 of the embodiment of FIG. 13.

Figure 18:
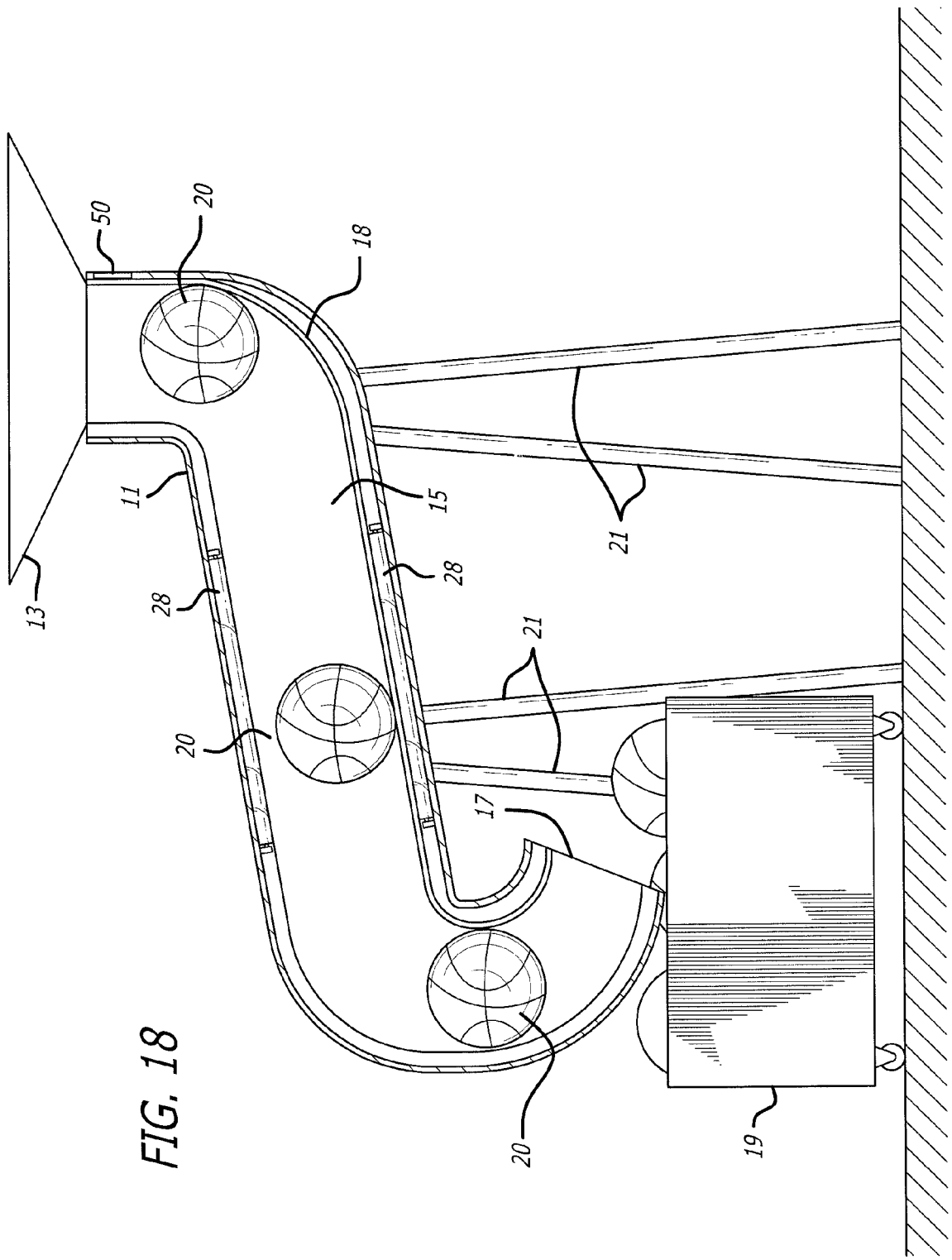

FIG. 18 is side sectional view of a third embodiment, the Inclined Drop Chute, mounted on legs. The proximity sensor powers/depowers the device. A cross sectional design such as FIG. 9 can be utilized.

Figure 19:
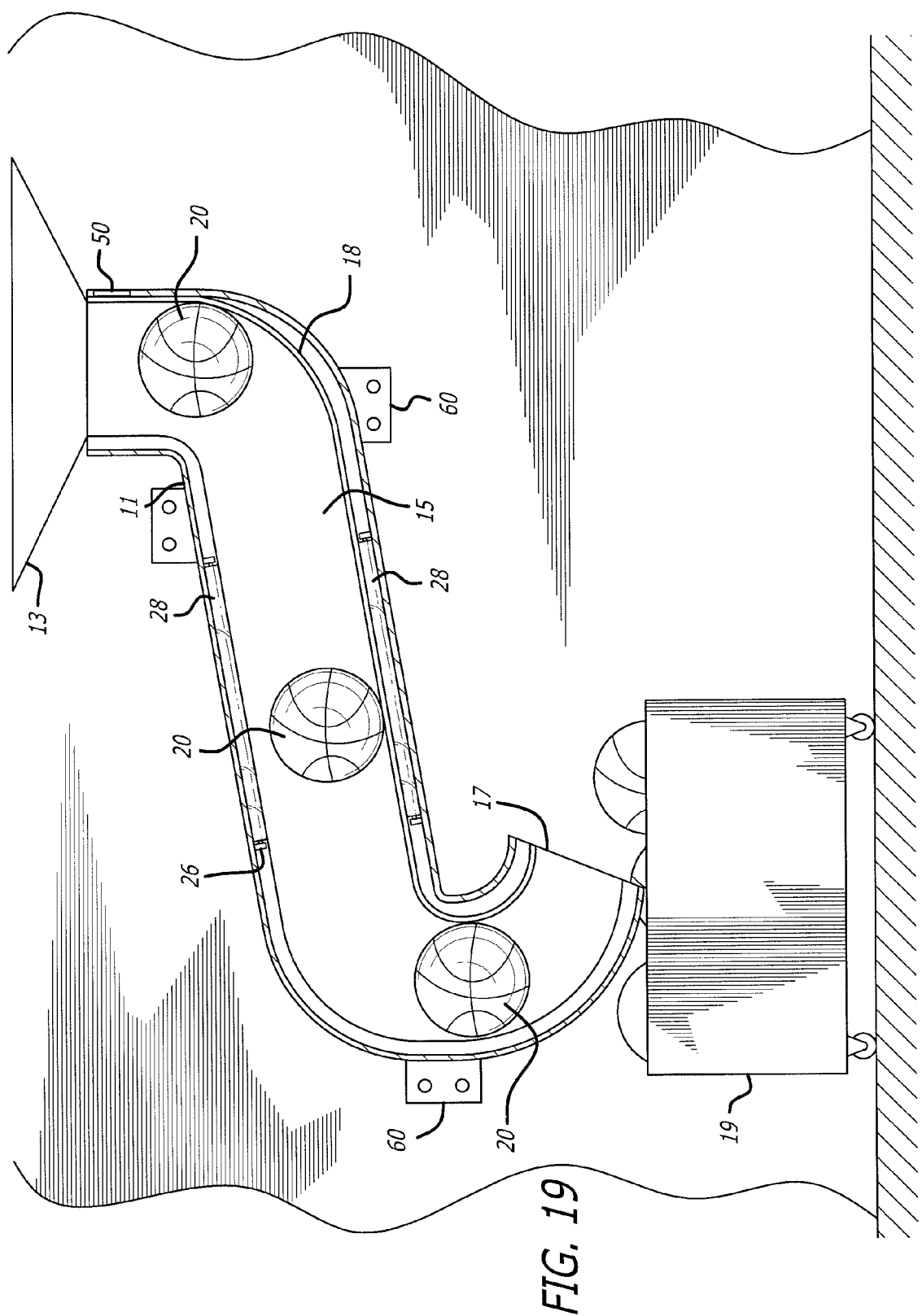

FIG. 19 is side sectional view of yet a different embodiment. This is another inclined drop chute embodiment, namely stationary and mounted on a wall.

Figure 20:
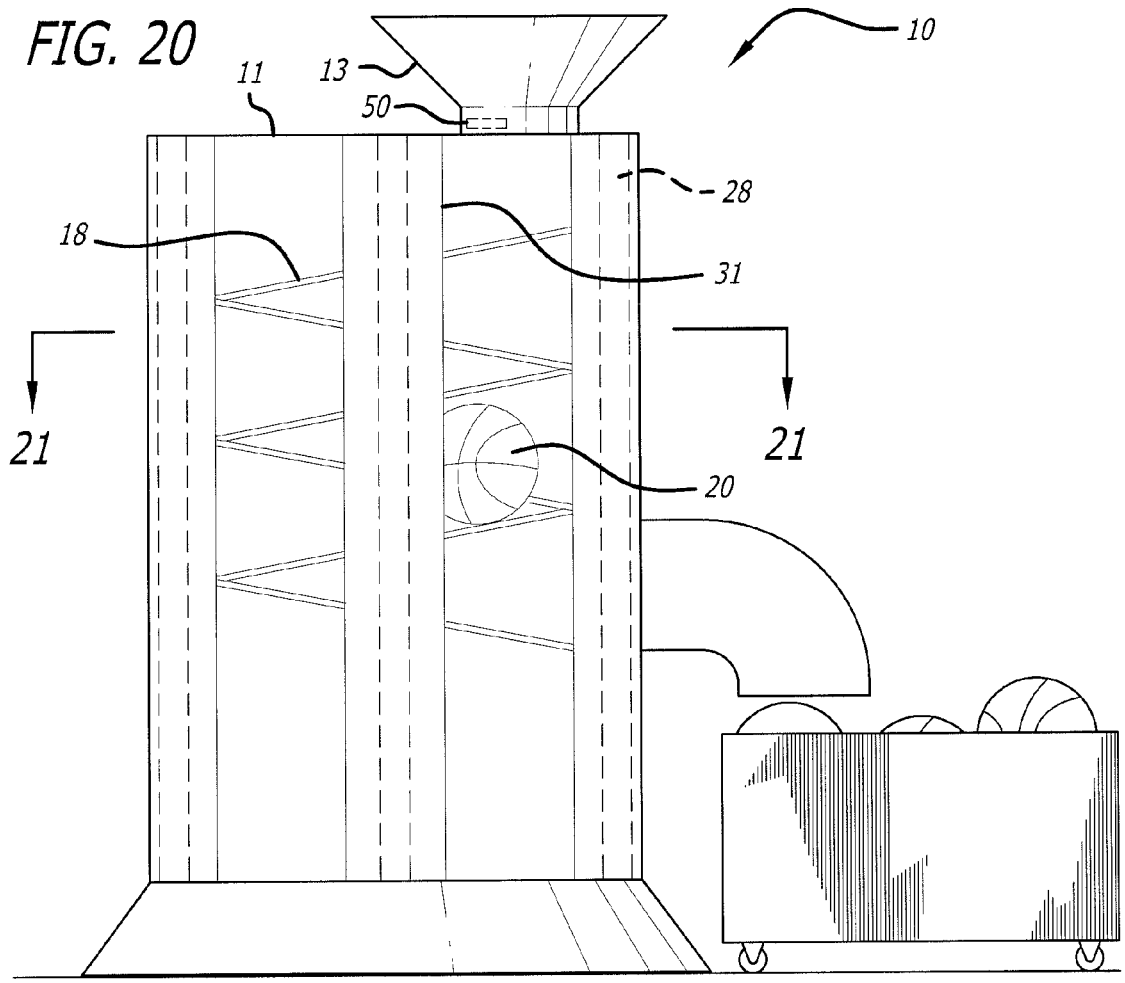

FIG. 20 is side view of fourth embodiment, the Double Helix Track, which is self standing.

Figure 21:
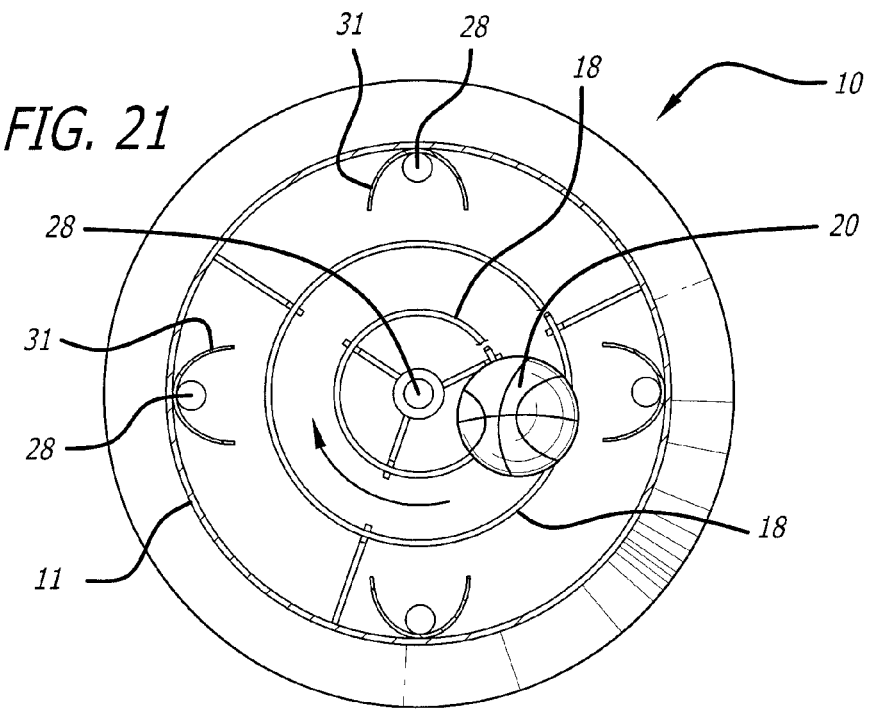

FIG. 21 is a top view of the embodiment of FIG. 20 along line 21-21 of FIG. 20.

DETAILED DESCRIPTION

Different embodiments are described, but should not be construed to be comprehensive or all-inclusive. The first embodiment provides a table top-pivoted design that is mechanically simple, lightweight and transportable. The housing/enclosure is elongated so that manual inclination of the housing/enclosure urges the ball to roll along tracks within the housing/enclosure, exposing all surfaces of the ball to the light source. The second embodiment provides a table top-internal roller design that rolls the ball within the stationary and compact housing/enclosure, utilizing a motor driven roller mechanism exposing all surfaces of the ball to the light source. The third embodiment provides a stand or wall mounted inclined drop-chute design that allows a plurality of balls to roll down an inclined essentially linear path through the housing/enclosure exposing all surfaces of the balls to the light source in rapid succession. The fourth embodiment provides a stand or wall mounted double helix track that allows a plurality of balls to roll down an inclined essentially helical path around a central light source and within peripheral light sources, through the housing/enclosure exposing all surfaces of the balls to the light source in rapid succession with a smaller "footprint" than the inclined drop chute design.

A system 10 for sterilizing a sports ball 20 comprises a housing 11; a door 14 for the housing 11 for opening and closing the housing 11 and for permitting manual location of a ball 20 in the housing 11. A sterilizing UVC light source 28 for sterilizing a ball 20 is placed inside the housing 11. The ball 20 is rotatable in the housing 11 relative to the one or more lights 28 such that essentially the entire surface of the ball 20 is subjected to exposure from the sterilizing light 28. There is a handle 36 for opening and closing the door 14 and can be to assist in carrying the system 10 as needed.

The housing 11 can include an elongated track 18 extendible from towards one end of the housing 11 towards the other end of the housing 11. The sterilizing light 28 can be elongated and located to extend from towards the one end of the housing 11 towards the other end of the housing 11. The housing 11 is elongated in length and sized such that the ball 20 can roll from a position towards the one end to a position towards the opposite end.

The track 18 can include a series or pair of rails 18, and the sterilizing light 28 can be located in a position to permit exposure of a ball at different positions of the ball as the ball moves on the rails, and this can be substantially in parallel with and between the rails 18. There can also be a series of rails 18 equidistantly arranged about an inside perimeter of the housing 11. There can be a series of sterilizing lights 26 located about an inside perimeter of the housing 11 and equidistantly spaced about the housing 11. The series of sterilizing lights 28 can be equidistantly spaced from each other and also be in parallel with and between the rails 18 of the track.

In some cases there is a support pivot element 16 provided on an outer surface of the housing and the pivot element 16 engages or rest on a horizontal surface 12. The pivot 16 permits the housing to be rocked about the pivot 16. The rocking permits a ball 20 inside the housing 11 to move reciprocally from end to end as the ball rotates in the housing 11. The pivot 16 includes a cut out 30 for accommodating the outer surface of the housing 11 in a stable manner.

In one different form of the device, the housing 11 includes one or more rollers 44 mounted on columns 46 on a base 48 of the housing 11. The sterilizing lights 28 are located around an internal surface of the housing 11. The housing 11 is more cubic in shape and sized such that a ball 20 can roll on the rollers 44 while inside the cavity 52 thereby ensuring exposure to the sterilizing lights 28. One or more of the rollers 44 is rotatable by a motor 40 under the action of a pulley belt 42 connected to the rotor shaft of the pulley and motor rotor shaft.

The series of rollers 44 is arranged so that at least one of the rollers 44 can be motorized thereby to rotate a ball located on one or more of the rollers 44. The sterilizing lights 28 can have connectors 26 and there can be reflectors 31 about each of the lights 28. The ballasts 27 are located in a position removed form the rails 18 and on the inside walls of the housing 11, such as behind the reflectors 31. There can be an activation switch 32 for the device 10, and the device itself is powered through a mains connected wire 22 from a mains power outlet. Alternatively suitable battery power packs 58 can be used. One or more indicators 38 can be related to a timing counter display relaying how long the sterilization has been operable and/or how much longer it needs to function to effect the requisite sterilization.

In another form the system for sterilizing multiple sports balls 20 at a time. The system 10 comprises a housing 11 with an opening mouth or funnel 13 for the housing 11 for permitting the manual location of balls 20 in the housing 11. There is one or more sterilizing lights 28 which can be aligned in series for sterilizing balls 20 placed in the housing 11. The balls 20 move and rotate in the housing 11 relative to the light 28 such that essentially the entire surface of the balls 20 are subjected to exposure from the sterilizing lights 28. The balls 20 roll down the chute 15 on rails 18 which are on the inside of the housing 11. A proximity sensor 50 recognizes the presence or absence of a ball and powers the light 28 for a predetermined time interval when a ball is present. An outlet from the housing is directed to a box or tray 19 for receiving one or more sterilized balls 20.

The housing can be for location on one or more support legs 21 such that the opening 13 is above the outlet 17. The balls 20 are movable under gravity between the opening 13 and outlet 17. The housing 11 includes an internal surface, which can be formed, at least in part, with a light reflective material.

The handle 36 can also permit portability of the housing 11, and there can be a portable power source 58 for the lights 28 and the device as a whole. There can be a timer for operation with a switch for the light thereby to regulate the amount of light to a ball.

Autoclaves generally sterilize objects utilizing a variety of germicidal means including chemical, heat, pressure, steam, gas, ionizing radiation and Ultraviolet "C" band (UVC) light. UVC lamps can produce germicidal ozone, but this is a secondary effect. The UVC band directly disrupts DNA and RNA and immediately disables cellular function and reproduction.

Ultra violet radiation in the 200-300 nanometer range is known to be extremely effective in destroying microorganisms such as an airborne and surface bacteria viruses, yeast and mold. Low-pressure light sources such as Mercury-arc germicide lamps are designed specifically to radiate mostly UV, typically radiating about 90 percent of the total radiated energy in the 253.7 nanometer range, which is close to the peak of the germicidal curve at 265 nanometers, considered the most lethal wavelength to microorganisms. The UV lights that are used in the housing produce predominantly germicidal effects and are not ozone producing. Preferably the light source produces only the germicidal effects and no ozone. This would be effective against sweat and the like associated with the ball being sterilized. The current disclosure does not rely on ozone production for the sterilizing effect. In fact, ozone production in a gym/sports environment may be undesirable.

UVC has some advantages over other sterilization means. It is inexpensive, rapid, and free of chemicals, heat, moisture, poisons, and penetrating ionizing radiation. The surface of the object is immediately sterile and safe to handle. UVC germ resistance has not emerged, despite decades of use, and mechanistically, is unlikely to occur.

UVC's main disadvantage is that its effect is limited only to those directly exposed surfaces, as well as the fluid/air through which it passes. UVC light has very limited penetration and effectiveness drops off rapidly with distance from the UVC source. Germs in a "shadow", crack or crevice are safe and will survive. High exposure to UVC light can also be harmful to human skin and eyes.

UVC is broadly known and commonly utilized for sterilization in water treating systems and air in Heating, Ventilation, Air Conditioning (HVAC) systems and operating rooms. UVC autoclaves are of limited utility as most objects (e.g. scissors) to be sterilized have non-exposable surfaces hidden in the "shade" away from the UVC source.

A rollable object, such as a ball handled in sports is ideally suited for such surface sterilization. Prior to the present disclosure, UVC has never previously been described for this purpose.

In a first embodiment, the "table top-external pivot" is mechanically simple, with no moving parts other than the door and associated mechanisms. It is lightweight, portable and may be placed on the scorer's table adjacent to the court of play. In a basketball or volleyball competition, only a single ball is used throughout the match, so this design accommodates only one ball. The disadvantage of this embodiment is that it must be of sufficient length to allow rolling the ball inside the housing/enclosure.

In a second embodiment, the "table top-internal roller" is similar to the table top-external pivot embodiment and is also for single ball and courtside use. Rather than the ball rolling within an elongated housing, a motor driven mechanism rotates the ball within the housing. The primary advantages of this embodiment is its compactness and more automated use. The disadvantage is that it is mechanically more complex, with added cost of manufacture and potential for mechanical failure.

In a third embodiment, the "inclined drop chute" is mechanically simple and intended for sterilization of multiple balls in rapid succession, as one would use in a practice, multi-team gym, or playground setting. The disadvantage is the size and weight of the unit decreasing portability. In a fourth embodiment, the "double helix track", is also mechanically simple and intended for sterilization of multiple balls in rapid succession, but features a more compact floor space efficient design ideally suited for a corner application First Embodiment (Table Top-External Pivot) FIGS. 1 to 12

Figure 1:
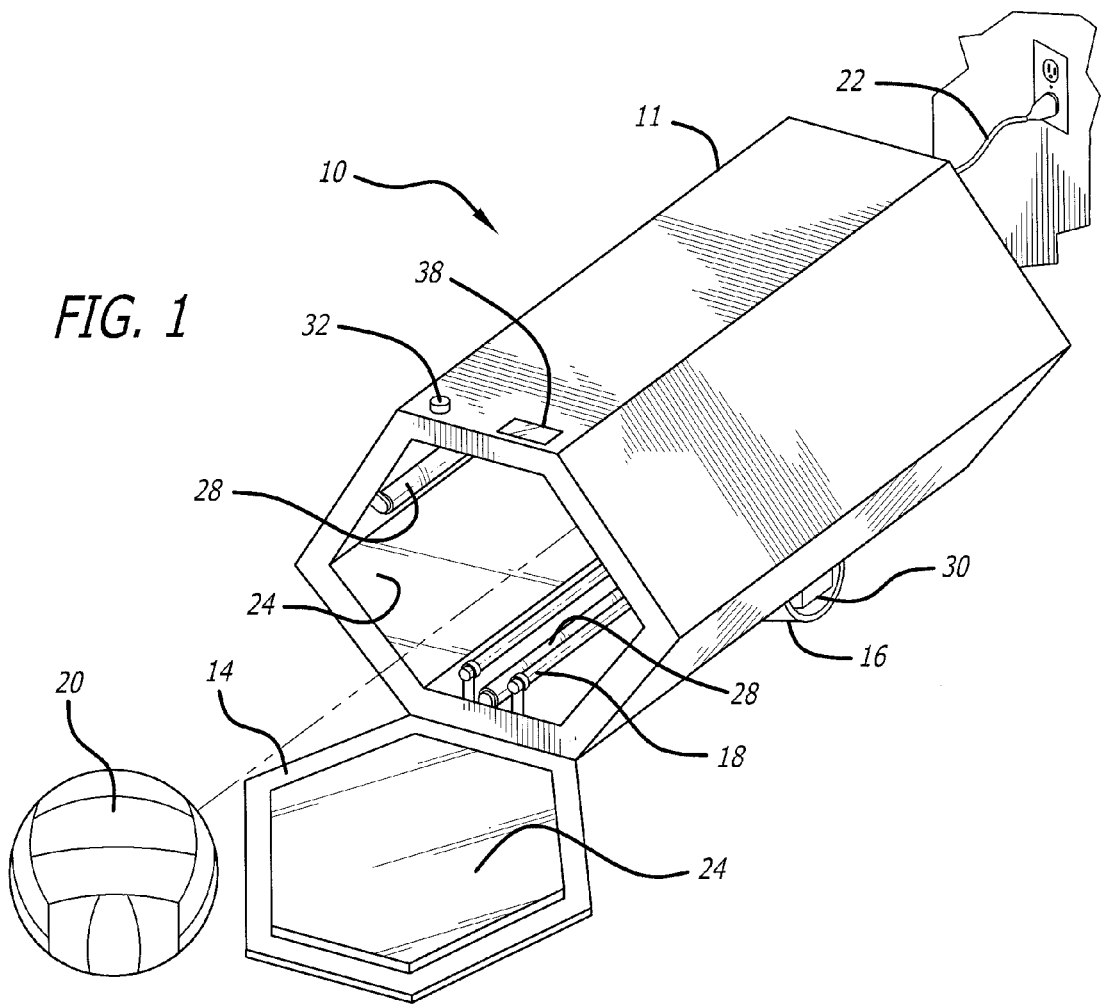

As shown in FIG. 1, a first embodiment (Table Top-pivot) of the disclosure consists of an elongated housing/enclosure with an access door on one end and an opposite closed end. The housing/enclosure is of sufficient cross sectional dimensions to accommodate the contents including a basketball, the track and the UVC source and sufficient length allowing rolling of the ball. The housing/enclosure is light proof, particularly in the UVC band.

The interior of the housing/enclosure is a reflective surface, such as reflective spectral aluminum. Further, the interior is supplied with angled or curved (e.g., parabolic with bulb at mathematical "focus") troffers efficiently reflecting the light at the ball. By joining the upper/central extensions of the troffers, the UVC bulbs are protected from physical damage by an errant ball. The interior may be configured geometrically to maximize exposure efficiency, depending upon the number and configuration of the UVC sources utilized.

An external pivot/roller, with a long axis perpendicular to the long axis of the housing/enclosure is located below the housing/enclosure about halfway along the housing/enclosure length. In this embodiment, the pivot structure contains the ballast for the fluorescent UVC source(s).

The device is powered via a cord for standard wall power source.

The door is hinged at the bottom. The door has a handle near its top that allows door opening and closing. The interior surface of the door is a reflective surface. The door has an interlocking mechanism, a multitude of which are known, that allows positive closure and allows powering of the UVC source only in the fully closed position.

The activation on/off switch/timer is located above the door and near the handle. If a manual switch, it is of the known "momentary on" configuration so that the device requires continuous action of the user to activate the UVC source. When the activation is stopped, the UVC source is depowered.

The housing/enclosure is provided with an activation indicator. Because UVC light is blocked by materials such as polycarbonate and glass transparent to visible light, a small window of this material assures the user that the ball is receiving the UVC light with no danger to the user.

Located within the housing/enclosure interior is a track on which the ball may roll the length of the housing/enclosure. In the preferred embodiment this track consists of two essentially parallel elongated members spaced for minimal rolling resistance while maintaining lateral stability.

Also located within the housing/enclosure is the UVC source(s). In the preferred embodiment, the UVC source is a pair of staggered "U" shaped fluorescent tubes located 90 degrees from each other with the "U" part of the bulb at the closed end of the housing/enclosure so the long axes of the tube and housing/enclosure are parallel. The sockets of the bulbs are on the door side of the housing/enclosure.

Figure 2:
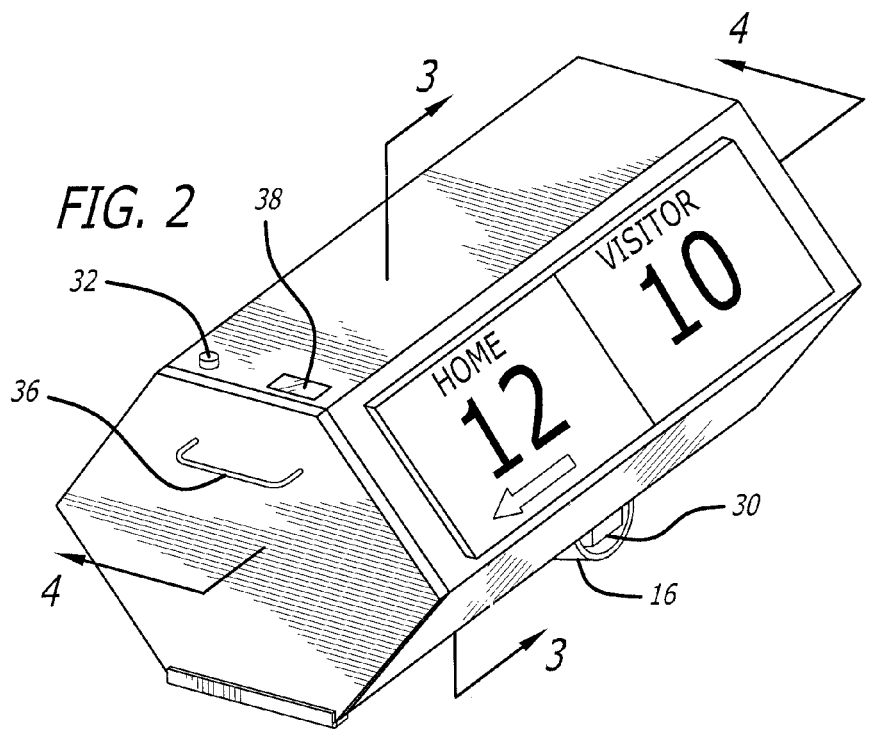
FIG. 2 is a perspective view of a first embodiment with the door closed. A display is shown on the outside wall of the housing.

The housing may have different cross sections, for instance, hexagonal as shown in FIGS. 1-3; cylindrical as shown in FIGS. 5-9, triangular as shown in FIG. 10 or square as shown in FIG. 11A-C. Other shapes are possible. A suitable pivot would be located under the housing.

A variation of the first embodiment is where the housing is mounted on a wall as shown in FIG. 13 where the housing has a wall mounting 60. As shown in FIG. 11 the light source can have different shapes. In FIG. 11A the light is an elongated tube with curvature to be U shaped or formed to be located along two sides and one end of the housing. In other forms instead of an elongated tube, there could be a series of self standing lights which can be located strategically in the housing and aligned as needed so that effective illumination is projected towards the path that the ball will travel. These are shown in FIGS. 11B and 11C.

Operation of the Table Top-External Pivot Embodiment

This embodiment is generally used in relatively close proximity to the court of play, on a horizontal surface such as a table or floor. The device is connected to the power supply.

To sterilize the ball, the door is opened by pulling the handle. The ball is placed onto the track and the door is closed. Opening the door deactivates the interlock mechanism and precludes powering the UVC source. Closing the door activates the interlock mechanism and allows powering of the UVC source.

The on/off switch is placed into the on position. The user checks the activation indicator to be certain the UVC source is powered on.

The entire housing/enclosure is tilted so the closed end rests on the horizontal surface. The ball inside the housing/enclosure rolls along the track to the closed end of the housing/enclosure urged by gravity. The ball is felt to impact the closed end. The entire housing/enclosure is then tilted so the door end rests on the horizontal surface. The ball inside the housing/enclosure rolls along the track to the door end of the housing/enclosure, urged by gravity. The ball is felt to impact the door end of the housing/enclosure.

The tilting procedure is repeated until sufficient time has elapsed for the acceptable level of sterilization. The final tilt should be with the door end of the housing/enclosure resting on the horizontal surface so the ball is easily retrieved.

Power is turned off by the timer or the hand switch. The Activation Indicator is checked to be certain the UVC source has been powered off. The door is opened and the ball, now sterilized, is removed and put back into play.

Second Embodiment (Table Top-Internal Roller) FIGS. 13 to 17

As shown in Figures, the housing is roughly cubicle and compact. A door with interlocks is provided. The interior of the housing is reflective and geometrically detailed to maximize exposure efficiency.

The UVC source (s) are arranged similar to that of the First Embodiment are shorter.

Three columns are provided spaced at the corners of an equilateral triangle at sufficient distance from each other to assure stability of the ball placed atop the columns. Each column is also covered with UVC reflective material. At the top of each column is a roller. The roller is narrow and cog wheel in configuration to minimize roller-ball contact to maximize UVC exposure. Two of the rollers are free to rotate passively and low friction. The third roller is attached, via a drive belt to a motor, located at the base of that column. The belt is contained within the column to minimize UVC degradation of the belt material.

Operation of the Table Top-Internal Roller Embodiment

This embodiment is generally used in relatively close proximity to the court of play, on a horizontal surface such as a table or floor. The device is connected to the power supply.

To sterilize the ball, the door is opened by pulling the handle. The ball is placed onto the three posts and the door is closed. Opening the door deactivates the interlock mechanism and precludes powering the UVC source. Closing the door activates the interlock mechanism and allows powering of the UVC source and motor.

The timer or on/off switch is powered on. The UVC sources as well as the motor are activated. The user checks the activation indicator to be certain the UVC source is powered on. The ball rotates on the rollers, exposing all surfaces.

When the preferred level of sterilization is achieved the UVC sources and motor are depowered via the timer or manual switch. The door is opened and the ball is removed and put back into play.

Third Embodiment (Inclined Drop Chute) FIGS. 18 to 19

As shown in FIGS. 18 and 19, the housing/enclosure may be on an accommodating movable stand or permanently wall mounted. The housing/enclosure is elongated and of any cross section shape, open on both ends. The housing/enclosure is mounted at an angle from the horizontal to allow a ball to roll at a pace that allows sufficient time for sterilization to occur. This configuration also discourages inadvertent UV light exposure of body parts of persons The upper end of the housing/enclosure has a bend so the upper opening is approximately horizontal and opens upward. The upper opening is expanded in a "hopper" configuration to ease placement of the balls into the housing/enclosure.

The lower end of the housing/enclosure has a bend to discourage inadvertent UV light exposure to body parts of persons and opens so as to allow the balls to exit the lower opening. The housing/enclosure is of sufficient cross sectional dimensions to accommodate the contents including a basketball, the track and the UVC source(s). The length is sufficient to allow the ball to roll past the UVC source to provide required sterilization exposure. An activation indicator is located along the presenting side of the housing/enclosure.

The inclined drop chute includes bends primarily to create an obstacle to hands and heads being exposed to the UVC sources. An alternative could be a straight shot and extended rail straight and in line above and below the chute. There could also be a turnstile, revolving doors, or flap type door used with this device. The location of the light is such as to being shielded from exposure to the outer housing.

The lower end opening is equipped with hooks to accommodate the hanging of a receiving net type ball bag in common use. The entire device should be hung/mounted at a height sufficient to permit a ball cart, also in common use, beneath the lower opening to receive and accommodate the sterilized balls.

A proximity sensor is contained within the housing/enclosure and situated in a manner that allows recognition of a ball within the housing/enclosure and recognizes the absence of a ball within the housing/enclosure. The presence of a ball within the housing/enclosure powers the UVC source. The absence of a ball with the housing/enclosure depowers the UVC source. An access door with interlock protection, is provided along the housing/enclosure to change bulbs when necessary Operation of the Inclined Drop Chute Embodiment The system includes a chute for receiving a ball. The chute includes an inlet located above and outlet, and a travel path between the inlet and outlet. The travel path includes at least one bend between the inlet and outlet, and preferably at least two bends. A ball traverses the path with a bend between the inlet and outlet, and the sterilizing light is located after the first bend. Where there are two bends the light is located before the second bend.

A multitude of balls are placed into the expanded upper opening. Gravity allows the balls to enter the housing/enclosure. The ball rolls down the track within the housing/enclosure where all surfaces of the ball are exposed to UVC light.

The ball then drops out the lower opening into a waiting receptacle such as a bag, cage or ball cart. The cart can have wheels so that sterilized balls in the cart can be easily moved to and from the outlet.

Fourth Embodiment (Double Helix Track) FIGS. 20 to 21

As shown in FIGS. 20 and 21, the housing/enclosure may be on an accommodating movable stand or permanently wall mounted. The housing/enclosure is substantially vertical and orientation with an upper hopper/opening and a lower outlet. The preferred housing is cylindrical with diameter of about 3 ball diameters to contain the internal construct.

Internally, there is a central core that consists of a UVC source arranged substantially along the central longitudinal axis of the cylinder. The track consists of two helical members that are parallel to each other and of different diameter. The tracks are mounted to the housing interior by a plurality of supports. The interior housing contains four additional UVC sources about its periphery with reflectors to maximize and focus the light toward the tracks.

The height of the device is sufficient to allow the ball to roll past the UVC sources to provide required sterilization exposure. An activation indicator is located along the presenting side of the housing/enclosure. A proximity sensor activates the UVC source when a ball is presented.

The lower end opening is equipped with hooks to accommodate the hanging of a receiving net type ball bag in common use. The entire device should be hung/mounted at a height sufficient to permit a ball cart, also in common use, to be located adjacent to the lower opening to receive and accommodate to the sterilized balls. The housing may contain a "bay" that allows the cart to be placed within the lower housing rather than adjacent to the housing as shown in FIG. 20.

A proximity sensor is contained within the housing/enclosure and situated in a manner that allows recognition of a ball within the housing enclosure and recognizes the absence of a ball within the housing/enclosure. The presence of a ball within the housing/enclosure powers the UVC source for a predetermined time interval. The absence of a ball within the housing/enclosure depowers the UVC source.

Operation of the Fourth (Double Helix Track) Embodiment

The system includes a chute for receiving a ball, the chute including an inlet located above and outlet, and a travel path between the inlet and outlet. The travel path includes a helical track between the inlet and outlet. A ball traverses the helical path between the inlet and outlet, and the sterilizing light is located outside the helical path and extends from an upper location to a lower location.

A multitude of balls are placed into the expanded upper opening. The proximity sensor activates the UVC source for a preset duration. Gravity allows the balls to enter the housing/enclosure. The ball rolls down the helical track within the housing/enclosure for all surfaces of the ball are exposed to the UVC light. The ball then drops out the lower opening into a waiting receptacle such as a bag, cage or ball cart.

Alternatives and Enhancements

In some cases, the embodiment using the "double helix track" is similar in principle to the inclined drop chute embodiment. However, the tracks wrap around a central core. This orientation is lager in diameter, but occupies a more compact footprint, and is ideally suited for a corner of a gym.

The disclosure provides for rapidly and efficiently sterilizing a rollable object such as a ball used in sports, including basketball and volleyball.

Common to the various embodiments is the housing/enclosure, the source(s) of UVC light, and a means of providing relative motion between the ball and the UVC source(s). The various alternatives described herein are but a few examples and are not to be construed as all inclusive, comprehensive or exhaustive.

The housing/enclosure can be of any exterior cross section, such as round, oval, polygonal, clover shaped, regular or irregular, symmetric or asymmetric. External padding may be applied or used as a structural element to provide protection to and from impact with players or balls. The housing exterior may display school/team logos or advertisements.

Add-on enhancements, such as alcohol based hand sanitizers may be affixed to the housing exterior. Accommodation for hand held sanitizing surface sprays may also be attached so the unit becomes a "sterilization station".

Although the table-top embodiments are intended for single ball use, providing a longer housing/enclosure can accommodate multiple balls.

A housing/enclosure can be designed "bottomless" with a handle on the top so that the ball is simply covered by the housing/enclosure as it sits on a horizontal surface such as a table. The ball can be exposed by moving the housing around, rolling the ball along the horizontal surface.

A manual or electronic scoreboard may be affixed to or incorporated into the housing/enclosure exterior.

The housing/enclosure interior may be of any reflective surface and color. Myriad configurations may be designed to optimize UVC ball exposure efficiency.

The descriptions of the table top models show doors hinged at the bottom and at the side. A variety of known door configurations, such as flaps, trap or rolling doors can also be utilized.

The door can be maintained closed through a variety of known mechanisms including spring hinges, magnetic and mechanical latches.

The door can be made to close automatically as the power/timer on/off switch is actuated. Similarly, the door may be configured to open automatically at the conclusion of the sterilization interval.

The power source shown is standard wall plug in whether 110 or 220 v, depending upon the local available supply. Battery operation may make the device more portable, although heavier and of limited duration use. Rechargeable/replaceable batteries are also anticipated.

The activation switch may be a simple hand on/off switch, an electro-mechanical timer, or similar circuitry for control of the power. Any means that prevents external escape of UVC is permissible.

Currently available UVC light sources are similar in size and shape to household fluorescent bulbs including straight cylindrical tubes, "U" shaped tubes and circular tubes. Depending upon the configuration of the disclosure any single style or combination of styles, including custom shape and sizes may be utilized. LED style UVC lamps may prove useful for this application.

Because the housing/enclosure is impenetrable to UVC, it is desirable to have an external indicator so the user knows the ball is being exposed. This can be achieved through a small window of glass or polycarbonate that is transparent to visible light, but impenetrable by UVC light. A simple visible light lamp can be wired in series to the UVC source.

A simple and inexpensive embodiment of the disclosure could use a strategically placed single bulb, rather than a plurality of bulbs as the UVC source. This would necessarily prolong the duration required for acceptable sterilization level.

A means of determining when bulbs require replacement may also be desirable. This could be a simple time logger device, or a UVC sensor that notifies the user when UVC output has dropped below acceptable levels.

The ballast should be located so as to be replaceable and not interfere with function of the device.

Currently, there are several varieties of UVC bulbs commercially available. The "cold cathode" variety is tolerant of multiple on/off cycles and comes up to full power very quickly, making it a good choice for the table top models. The "hot cathode" variety are intended for prolonged or continuous use with a long life, and may be a good choice for the "Inclined Drop Chute" embodiment which may be left on for hours at a time.

The embodiments described herein provide distinct means of exposing all surfaces of the ball to the UVC source by providing relative motion between the ball and the UVC source. This can be accomplished by moving the entire housing/enclosure to urge the rolling (revolution and translation) of the ball, providing a mechanism (motor, elastic, hand driven) to allow the ball to revolve around one or more axes without translation, and a pass-through design. Translation without rotation can also achieve this purpose. A myriad of configurations are possible to achieve this effect. Similarly, configurations wherein the ball remains stationary and the UVC source moves relative to the ball can also be designed.

Specificities for multiple embodiments have been described. These should not be construed as limitations on the scope, but rather as an exemplification of several embodiments thereof. These embodiments are presented as a demonstration that many other variations are possible. While the apparatus, method and system have been described in terms of what are presently considered to be the most practical and preferred embodiments, it is to be understood that the disclosure need not be limited to the disclosed embodiments.

For instance, although the disclosure has considered lights essentially parallel with the rails, there could be other formats. In one alternative, there could be 14 inch diameter round light tubes in series every 4 inches along the course of the housing. In this event the lights would be perpendicular to the track. Alternatively, there could be a single helical bulb, and the ball passes through the bulb interior. For instance there could be a double helix design of lights, and the bulbs in that case are about 30 degrees angled to the tracks. Some of these variations of the light sources are shown in FIGS. 11A, 11B and 11C. In other cases instead of the lights being arranged in a parallel fashion relative to the tracks, the lights may be arranged in a non-parallel relatively random manner in relationship with the tracks.

It is intended to cover various modifications and similar arrangements included within the spirit and scope of the claims, the scope of which should be accorded the broadest interpretation so as to encompass all such modifications and similar structures. For instance, the lights can be equidistant or non equidistant relative to each other. The present disclosure includes any and all embodiments of the following claims.

The invention claimed is:

1. A system for sterilizing a sports ball comprising: a housing; a door for the housing for opening and closing the housing and for permitting manual location of a ball in the housing; a sterilizing light for sterilizing a ball placed in the housing, the ball being rotatable in the housing relative to the light such that essentially the entire surface of the ball is subjected to exposure from the sterilizing light, and wherein the housing includes an elongated track extending from towards one end of the housing towards another end of the housing, and the sterilizing light is elongated from towards one end of the housing towards another end of the housing, and wherein the housing is sized such that a ball is rollable from a position towards one end to a position towards an opposite end.

2. The system as claimed in claim 1 wherein the track includes a series of rails, and wherein the sterilizing light is located substantially in a position to permit exposure of a ball at different positions of the ball as the ball moves on the rails.

3. A system for sterilizing a sports ball comprising: a housing; a door for the housing for opening and closing the housing and for permitting manual location of a ball in the housing; a sterilizing light for sterilizing a ball placed in the housing, the ball being rotatable in the housing relative to the light such that essentially the entire surface of the ball is subjected to exposure from the sterilizing light, and including a series of rails equidistantly arranged about an inside perimeter of the housing, and including a series of sterilizing lights located about an inside perimeter of the housing and equidistantly spaced.

4. The system as claimed in claim 2 wherein the series of rails are equidistantly arranged about an inside perimeter of the housing, and including a series of sterilizing lights located about an inside perimeter of the housing and equidistantly spaced, and being parallel with the rails.

5. A system for sterilizing a sports ball comprising: a housing; a door for the housing for opening and closing the housing and for permitting manual location of a ball in the housing; a sterilizing light for sterilizing a ball placed in the housing, the ball being rotatable in the housing relative to the light such that essentially the entire surface of the ball is subjected to exposure from the sterilizing light, and including a support pivot provided on an outer surface of the housing, whereby the pivot permits the housing to be rocked about the pivot, and wherein the rocking permits a ball inside the housing to move reciprocally from end to end as the ball rotates in the housing.

6. A system for sterilizing a sports ball comprising: a housing; a door for the housing for opening and closing the housing and for permitting manual location of a ball in the housing; a sterilizing light for sterilizing a ball placed in the housing, the ball being rotatable in the housing relative to the light such that essentially the entire surface of the ball is subjected to exposure from the sterilizing light, and wherein the housing includes a roller, and the sterilizing light is located around an internal surface of the housing, and wherein the housing is sized such that a ball is rollable on the roller thereby ensuring expose to the sterilizing light.

7. The system as claimed in claim 1 including a series of rollers and wherein at least one of the rollers is movable thereby to rotate a ball located on the rollers, and wherein the sterilizing light is located within the inside surface so as to permit a rotatable ball to be exposed to the sterilizing light.

8. A system for sterilizing a sports ball comprising: a housing; an opening for the housing for permitting manual location of a ball in the housing; a sterilizing light for sterilizing a ball placed in the housing, the ball being rotatable in the housing relative to the light such that essentially the entire surface of the ball is subjected to exposure from the sterilizing light, and an outlet from the housing, and a receptacle for receiving a sterilized ball.

9. The system as claimed in claim 8 wherein the housing includes an elongated track extending from towards one end of the housing towards another end of the housing, and the sterilizing light is elongated from towards one end of the housing towards another end of the housing, and wherein the housing is sized such that a ball is rollable from a position towards one end to a position towards an opposite end.

10. The system as claimed in claim 9 wherein the track includes a series of rails, and wherein the sterilizing light is located substantially in parallel with the rails.

11. The system as claimed in claim 8 including a series of rails equidistantly arranged about an inside perimeter of the housing, and including a series of sterilizing lights located about an inside perimeter of the housing and equidistantly spaced.

12. The system as claimed in claim 10 wherein the series of rails are equidistantly arranged about an inside perimeter of the housing, and including a series of sterilizing lights located about an inside perimeter of the housing and equidistantly spaced, and in a position to permit exposure of a ball at different positions of the ball as the ball moves on the rails.

13. The system as claimed in claim 8 wherein the housing is for location on a support such that the opening is above the outlet, such the ball is movable under gravity between the opening and outlet.

14. The system as claimed in claim 1 wherein the housing includes an internal surface, the internal surface being formed, at least in part, with a UVC light reflective material.

15. The system as claimed in claim 5 wherein the housing includes an internal surface, the internal surface being formed, at least in part, with a UVC light reflective material.

16. The system as claimed in claim 6 wherein the housing includes an internal surface, the internal surface being formed, at least in part, with a UVC light reflective material.

17. The system as claimed in claim 8 wherein the housing includes an internal surface, the internal surface being formed, at least in part, with a UVC light reflective material.

18. The system as claimed in claim 1 including a handle to permit portability of the housing, and a portable power source for the system.

19. The system as claimed in claim 1 including a timer for operation with a switch for the light thereby to regulate the duration of light to which a ball is subject.

20. The system as claimed in claim 1 including a chute for receiving a ball, the chute including an inlet located above and outlet, and a travel path between the inlet and outlet, the travel path including at least one bend between the inlet and outlet, and preferably at least two bends, such that a ball traverses the path with a bend between the inlet and outlet, and the sterilizing light is located after the first bend, and where there are two bends before the second bend, and the light being shielded from exposure to the housing.

21. The system as claimed in claim 1 including a chute for receiving a ball, the chute including an inlet located above and outlet, and a travel path between the inlet and outlet, the travel path including a helical track between the inlet and outlet, such a ball traverses the helical path between the inlet and outlet, and the sterilizing light is located selectively at least one of outside or inside of the helical path and extends from an upper location to a lower location.

22. The system as claimed in claim 1 wherein the light source is selected to be at least one of an elongated straight light, one or more discreet separate round bulbs, a u-elongated shaped source or a helical shaped source, and wherein the lights are selectively equidistant or non equidistant relative to each other.

23. The system as claimed in claim 1 including a mounting for connection to a wall, the mounting selectively including a pivot mechanism, and selectively there being limiting stops located at angles sufficient to allow the housing to tilt.

24. The system as claimed in claim 1 wherein the track includes a rail, and wherein the sterilizing light is located substantially in a position to permit exposure of a ball at different positions of the ball as the ball moves on the rail.

25. A system for sterilizing a sports ball comprising: a housing; an opening for the housing for permitting manual location of a ball in the housing; a sterilizing light for sterilizing a ball placed in the housing, the ball being rotatable in the housing relative to the light such that essentially the entire surface of the ball is subjected to exposure from the sterilizing light, and wherein the housing includes an elongated track extending from towards one end of the housing towards another end of the housing, and the sterilizing light is elongated from towards one end of the housing towards another end of the housing, and wherein the housing is sized such that a ball is rollable from a position towards one end to a position towards an opposite end.

26. The system as claimed in claim 25 wherein the track includes a rail, and wherein the sterilizing light is located substantially in a position to permit exposure of a ball at different positions of the ball as the ball moves on the rail.

27. The system as claimed in claim 25 including a chute for receiving the ball, the chute including the opening located above the housing and an outlet, and the elongated track including at least one bend between the opening and outlet, and preferably at least two bends, such that a ball traverses the path with a bend between the opening and outlet, and the sterilizing light is located after the first bend, and where there are two bends before the second bend, and the light being shielded from exposure to the housing.

28. The system as claimed in claim 25 including a receptacle for receiving a sterilized ball.

\* \* \* \* \*